US011642249B2

(12) United States Patent
Schneider et al.

(10) Patent No.: US 11,642,249 B2
(45) Date of Patent: May 9, 2023

(54) METHODS AND APPARATUSES FOR MAKING ELASTOMERIC LAMINATES WITH ELASTIC STRANDS PROVIDED WITH A SPIN FINISH

(71) Applicant: The Procter & Gamble Company, Cincinnati, OH (US)

(72) Inventors: Uwe Schneider, Cincinnati, OH (US); Joseph Allen Eckstein, Sunman, IN (US)

(73) Assignee: The Procter & Gamble Company, Cincinnati, OH (US)

(*) Notice: Subject to any disclaimer, the term of this patent is extended or adjusted under 35 U.S.C. 154(b) by 840 days.

(21) Appl. No.: 15/831,464

(22) Filed: Dec. 5, 2017

(65) Prior Publication Data

US 2018/0168877 A1  Jun. 21, 2018

Related U.S. Application Data

(60) Provisional application No. 62/581,278, filed on Nov. 3, 2017, provisional application No. 62/553,171, filed on
(Continued)

(51) Int. Cl.
*A61F 13/15*  (2006.01)
*A61F 13/49*  (2006.01)
(Continued)

(52) U.S. Cl.
CPC .... *A61F 13/15593* (2013.01); *A61F 13/4902* (2013.01); *A61F 13/49061* (2013.01);
(Continued)

(58) Field of Classification Search
CPC .......... A61F 13/15593; A61F 13/15699; A61F 13/49011; A61F 13/49012;
(Continued)

(56) References Cited

U.S. PATENT DOCUMENTS 3,113,225 A    12/1963  Kleesattel et al.
3,434,189 A *   3/1969  Buck ....................... D02J 1/221
                                                    264/78
(Continued)

FOREIGN PATENT DOCUMENTS

CA      2158790         3/1996
CN      1276196 A       6/1999
(Continued)

OTHER PUBLICATIONS

PCT International Search Report, dated Mar. 12, 2018, 12 pages.
(Continued)

*Primary Examiner* — John L Goff, II
(74) *Attorney, Agent, or Firm* — Charles R. Matson

(57) ABSTRACT

The present disclosure relates to methods for making elastomeric laminates that may be used as components of absorbent articles. The methods and apparatuses may be configured with a plurality of elastic strands wound onto a beam, wherein one or more elastic strands comprises a spin finish. During assembly of an elastomeric laminate, the beam is rotated to unwind the elastic strands from the beam. A portion of the spin finish may be removed from the advancing elastic strand with a spin finish removal apparatus. The spin finish removal apparatus may be configured to apply detergent to an advancing elastic strand and may also wipe and/or dry the advancing elastic strand. The treated stretched elastic strand may then be connected between a first substrate and a second substrate. In some configurations, adhesive may be applied to the treated the elastic strand, the first substrate, and/or the second substrate.

8 Claims, 10 Drawing Sheets

Related U.S. Application Data on Sep. 1, 2017, provisional application No. 62/553,538, filed on Sep. 1, 2017, provisional application No. 62/553,149, filed on Sep. 1, 2017, provisional application No. 62/483,965, filed on Apr. 11, 2017, provisional application No. 62/436,589, filed on Dec. 20, 2016.

(51) Int. Cl.

| | |
|---|---|
| B32B 27/12 | (2006.01) |
| D01F 6/04 | (2006.01) |
| A61F 13/53 | (2006.01) |
| D01D 5/08 | (2006.01) |
| B29C 65/08 | (2006.01) |
| B29C 65/48 | (2006.01) |
| B29L 31/48 | (2006.01) |
| B05C 1/08 | (2006.01) |
| B32B 37/14 | (2006.01) |
| B65H 39/16 | (2006.01) |
| B65H 51/30 | (2006.01) |
| B29C 65/00 | (2006.01) |
| B29C 65/74 | (2006.01) |
| B29K 701/12 | (2006.01) |
| A61F 13/64 | (2006.01) |
| A61F 13/84 | (2006.01) |
| B32B 5/04 | (2006.01) |
| B32B 37/00 | (2006.01) |
| B32B 37/12 | (2006.01) |
| D04H 3/12 | (2006.01) |
| A61F 13/56 | (2006.01) |
| B32B 37/22 | (2006.01) |
| A61F 13/513 | (2006.01) |

(52) U.S. Cl.
CPC ... *A61F 13/15601* (2013.01); *A61F 13/15699* (2013.01); *A61F 13/15739* (2013.01); *A61F 13/15764* (2013.01); *A61F 13/49012* (2013.01); *A61F 13/49015* (2013.01); *A61F 13/49017* (2013.01); *A61F 13/49019* (2013.01); *A61F 13/53* (2013.01); *A61F 13/5622* (2013.01); *A61F 13/64* (2013.01); *A61F 2013/1552* (2013.01); *A61F 2013/1591* (2013.01); *A61F 2013/15292* (2013.01); *A61F 2013/15373* (2013.01); *A61F 2013/15406* (2013.01); *A61F 2013/15447* (2013.01); *A61F 2013/15552* (2013.01); *A61F 2013/15869* (2013.01); *A61F 2013/15918* (2013.01); *A61F 2013/15959* (2013.01); *A61F 2013/49022* (2013.01); *A61F 2013/49025* (2013.01); *A61F 2013/49026* (2013.01); *A61F 2013/49074* (2013.01); *A61F 2013/49092* (2013.01); *A61F 2013/49093* (2013.01); *A61F 2013/51322* (2013.01); *A61F 2013/53043* (2013.01); *A61F 2013/530343* (2013.01); *A61F 2013/8497* (2013.01); *B05C 1/0808* (2013.01); *B29C 65/08* (2013.01); *B29C 65/086* (2013.01); *B29C 65/48* (2013.01); *B29C 65/74* (2013.01); *B29C 66/01* (2013.01); *B29C 66/344* (2013.01); *B29C 66/8141* (2013.01); *B29C 66/83411* (2013.01); *B29K 2701/12* (2013.01); *B29K 2995/0046* (2013.01); *B29L 2031/4878* (2013.01); *B32B 5/04* (2013.01); *B32B 27/12* (2013.01); *B32B 37/0053* (2013.01); *B32B 37/12* (2013.01); *B32B 37/144* (2013.01); *B32B 37/22* (2013.01); *B32B 2305/20* (2013.01); *B32B 2307/51* (2013.01); *B32B 2307/726* (2013.01); *B32B 2555/02* (2013.01); *B65H 39/16* (2013.01); *B65H 51/30* (2013.01); *C08J 2300/26* (2013.01); *D01D 5/08* (2013.01); *D01F 6/04* (2013.01); *D04H 3/12* (2013.01)

(58) Field of Classification Search
CPC .......... A61F 13/49014; A61F 13/49015; A61F 13/49017; A61F 13/49019; A61F 13/4902; A61F 13/49061; A61F 13/51464; A61F 13/496; A61F 13/51478; A61F 2013/49025; A61F 2013/49026; A61F 2013/49028; A61F 2013/49031; A61F 2013/51322; A61F 2013/1591; D01D 5/08; D02G 3/32; D04H 3/005; D04H 3/12; B29C 65/08; B29C 65/083; B29C 65/085; B29C 65/086; B29C 65/088; B29C 65/74; B29C 65/743; B29C 65/7435; B29C 65/7443; B29C 65/7455; B29C 66/344; B32B 37/0053; B32B 27/12; C08J 2300/26
See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long et al. |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa et al. |
| 4,525,905 A | 7/1985 | Bogucki-Land |
| 4,610,678 A | 9/1986 | Weisman et al. |
| 4,640,859 A | 2/1987 | Hansen |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert et al. |
| 4,776,911 A | 10/1988 | Uda et al. |
| 4,795,454 A | 1/1989 | Dragoo |
| 4,834,735 A | 5/1989 | Alemany et al. |
| 4,854,984 A | 8/1989 | Ball et al. |
| 4,888,231 A | 12/1989 | Angstadt |
| 4,909,803 A | 3/1990 | Aziz et al. |
| 4,940,464 A | 7/1990 | Van Gompel et al. |
| 4,984,584 A | 1/1991 | Hansen |
| 5,003,676 A | 4/1991 | McFalls |
| 5,060,881 A | 10/1991 | Bogucki-Land |
| 5,092,861 A | 3/1992 | Nomura et al. |
| 5,110,403 A | 5/1992 | Ehlert |
| 5,167,897 A | 12/1992 | Weber et al. |
| 5,246,433 A | 9/1993 | Hasse et al. |
| 5,334,289 A | 8/1994 | Trokhan et al. |
| 5,342,341 A | 8/1994 | Igaue |
| 5,360,420 A | 11/1994 | Cook et al. |
| 5,393,360 A | 2/1995 | Bridges et al. |
| 5,413,849 A | 5/1995 | Austin et al. |
| 5,514,523 A | 5/1996 | Trokhan |
| 5,531,729 A | 7/1996 | Coles |
| 5,558,658 A | 9/1996 | Menard et al. |
| 5,562,646 A | 10/1996 | Goldman et al. |
| 5,569,234 A | 10/1996 | Buell et al. |
| 5,575,874 A | 11/1996 | Griesbach, III et al. |
| 5,599,335 A | 2/1997 | Goldman et al. |
| 5,599,420 A | 2/1997 | Yeo et al. |
| 5,628,097 A | 5/1997 | Benson et al. |
| 5,643,588 A | 7/1997 | Roe et al. |
| 5,643,653 A | 7/1997 | Griesbach, III et al. |
| 5,669,894 A | 9/1997 | Goldman et al. |
| 5,674,216 A | 10/1997 | Buell et al. |
| 5,702,551 A | 12/1997 | Huber et al. |

(56) References Cited

U.S. PATENT DOCUMENTS

| | | |
|---|---|---|
| 5,775,380 A | 7/1998 | Roelstraete et al. |
| 5,827,259 A | 10/1998 | Laux |
| 5,858,504 A | 1/1999 | Steven |
| 5,887,322 A | 3/1999 | Hartzheim et al. |
| 5,895,623 A | 4/1999 | Trokhan |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |
| 5,993,433 A | 11/1999 | St. Louis |
| 5,997,521 A | 12/1999 | Robles et al. |
| 6,036,796 A | 3/2000 | Halbert et al. |
| 6,043,168 A | 3/2000 | Colman |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,139,941 A | 10/2000 | Jankevics et al. |
| 6,153,209 A | 11/2000 | Vega et al. |
| 6,248,195 B1 | 6/2001 | Schmitz |
| 6,248,197 B1 | 6/2001 | Nakanishi et al. |
| 6,291,039 B1 | 9/2001 | Combe et al. |
| 6,319,239 B1 | 11/2001 | Daniels et al. |
| 6,361,638 B2 | 3/2002 | Takai |
| 6,383,431 B1 | 5/2002 | Dobrin et al. |
| 6,395,957 B1 | 5/2002 | Chen et al. |
| 6,410,129 B2 | 6/2002 | Zhang et al. |
| 6,426,444 B2 | 7/2002 | Roe et al. |
| 6,475,600 B1 | 11/2002 | Morman et al. |
| 6,478,785 B1 | 11/2002 | Ashton et al. |
| 6,482,191 B1 | 11/2002 | Roe et al. |
| 6,508,641 B1 | 1/2003 | Kubik |
| 6,545,197 B1 | 4/2003 | Muller et al. |
| 6,554,815 B1 | 4/2003 | Umebayashi |
| 6,586,652 B1 | 7/2003 | Roe et al. |
| 6,617,016 B2 | 9/2003 | Zhang et al. |
| 6,627,787 B1 | 9/2003 | Roe et al. |
| 6,632,504 B1 | 10/2003 | Gillespie |
| 6,645,330 B2 | 11/2003 | Pargass et al. |
| 6,673,418 B1 | 1/2004 | DeOlivera et al. |
| 6,676,054 B2 | 1/2004 | Heaney et al. |
| 6,702,798 B2 | 3/2004 | Christoffel |
| 6,790,798 B1 | 9/2004 | Suzuki et al. |
| 6,821,301 B2 | 11/2004 | Azuse et al. |
| 6,825,393 B2 | 11/2004 | Roe et al. |
| 6,861,571 B1 | 3/2005 | Roe et al. |
| 7,008,685 B2 | 3/2006 | Groitzsch et al. |
| 7,118,558 B2 | 10/2006 | Wu et al. |
| 7,465,367 B2 | 12/2008 | Day |
| 7,569,039 B2 | 8/2009 | Matsuda et al. |
| 7,582,348 B2 | 9/2009 | Ando et al. |
| 7,642,398 B2 | 1/2010 | Jarpenberg et al. |
| 7,708,849 B2 | 5/2010 | McCabe |
| 7,777,094 B2 | 8/2010 | Mori et al. |
| 7,861,756 B2 | 1/2011 | Jenquin et al. |
| 7,878,447 B2 | 2/2011 | Hartzheim |
| 7,901,393 B2 | 3/2011 | Matsuda et al. |
| 7,905,446 B2 | 3/2011 | Hartzheim |
| 7,954,213 B2 | 6/2011 | Mizutani |
| 8,093,161 B2 | 1/2012 | Bansal et al. |
| 8,143,177 B2 | 3/2012 | Noda et al. |
| 8,186,296 B2 | 5/2012 | Brown et al. |
| 8,226,625 B2 | 7/2012 | Turner et al. |
| 8,308,706 B2 | 11/2012 | Fukae |
| 8,377,554 B2 | 2/2013 | Martin et al. |
| 8,388,594 B2 | 3/2013 | Turner et al. |
| 8,440,043 B1 | 5/2013 | Schneider et al. |
| 8,585,666 B2 | 11/2013 | Weisman et al. |
| 8,647,319 B2 | 2/2014 | Een et al. |
| 8,729,332 B2 | 5/2014 | Takahashi et al. |
| 8,778,127 B2 | 7/2014 | Schneider et al. |
| 8,853,108 B2 | 10/2014 | Ahoniemi et al. |
| 8,906,275 B2 | 12/2014 | Davis et al. |
| 8,939,957 B2 | 1/2015 | Raycheck et al. |
| 9,005,392 B2 | 4/2015 | Schneider et al. |
| 9,039,855 B2 | 5/2015 | Schneider et al. |
| 9,050,213 B2 | 6/2015 | LaVon et al. |
| 9,156,648 B2 | 10/2015 | Yamamoto |
| 9,168,182 B2 | 10/2015 | Hargett et al. |
| 9,198,804 B2 | 12/2015 | Nakamura et al. |
| 9,226,861 B2 | 1/2016 | LaVon et al. |
| 9,248,054 B2 | 2/2016 | Brown et al. |
| 9,265,672 B2 | 2/2016 | Brown et al. |
| 9,295,590 B2 | 3/2016 | Brown et al. |
| 9,370,775 B2 | 6/2016 | Harvey |
| 9,440,043 B2 | 9/2016 | Schneider et al. |
| 9,453,303 B2 | 9/2016 | Aberg et al. |
| 9,539,735 B2 | 1/2017 | Ferguson et al. |
| 9,732,454 B2 | 8/2017 | Davis et al. |
| 9,758,339 B2 | 9/2017 | Yanez, Jr. et al. |
| 9,795,520 B2 | 10/2017 | Kaneko et al. |
| 9,877,876 B2 | 1/2018 | Huang et al. |
| 10,190,244 B2 | 1/2019 | Ashraf et al. |
| 10,596,045 B2 | 3/2020 | Koshijima |
| 10,792,194 B2 | 10/2020 | Hohm |
| 11,129,753 B2 * | 9/2021 | Schneider ......... A61F 13/15593 |
| 2001/0030014 A1 | 10/2001 | Kwok |
| 2002/0026660 A1 | 3/2002 | Goda |
| 2002/0046802 A1 | 4/2002 | Tachibana et al. |
| 2002/0072723 A1 | 6/2002 | Ronn |
| 2002/0099347 A1 | 7/2002 | Chen et al. |
| 2002/0103469 A1 | 8/2002 | Chen et al. |
| 2002/0134067 A1 | 9/2002 | Heaney et al. |
| 2002/0153271 A1 | 10/2002 | McManus et al. |
| 2002/0177829 A1 | 11/2002 | Fell et al. |
| 2003/0024052 A1 * | 2/2003 | Azuse ................ D06M 13/463 |
| | | 8/115.51 |
| 2003/0044585 A1 | 3/2003 | Taylor |
| 2003/0070780 A1 | 4/2003 | Chen |
| 2003/0087056 A1 | 5/2003 | Ducker |
| 2003/0093045 A1 | 5/2003 | Jensen |
| 2003/0119404 A1 | 6/2003 | Belau et al. |
| 2003/0125687 A1 | 7/2003 | Gubernick et al. |
| 2003/0144643 A1 | 7/2003 | Jarpenberg |
| 2003/0203162 A1 | 10/2003 | Christopher et al. |
| 2003/0233082 A1 | 12/2003 | Kline et al. |
| 2004/0006323 A1 | 1/2004 | Hall et al. |
| 2004/0030317 A1 | 2/2004 | Torigoshi |
| 2004/0059309 A1 | 3/2004 | Nortman |
| 2004/0097895 A1 | 5/2004 | Busam et al. |
| 2004/0127881 A1 | 7/2004 | Stevens et al. |
| 2004/0133180 A1 | 7/2004 | Mori et al. |
| 2004/0158212 A1 | 8/2004 | Ponomarenko et al. |
| 2004/0158217 A1 | 8/2004 | Wu et al. |
| 2004/0219854 A1 | 11/2004 | Groitzsch et al. |
| 2004/0230171 A1 | 11/2004 | Ando et al. |
| 2005/0013975 A1 | 1/2005 | Brock et al. |
| 2005/0107764 A1 | 5/2005 | Matsuda et al. |
| 2005/0148971 A1 | 7/2005 | Kuroda et al. |
| 2005/0230037 A1 | 10/2005 | Jenquin et al. |
| 2005/0244640 A1 * | 11/2005 | Riswick ................ A61L 15/42 |
| | | 428/375 |
| 2005/0267431 A1 | 12/2005 | Sasaki |
| 2006/0047260 A1 | 3/2006 | Ashton et al. |
| 2006/0069373 A1 | 3/2006 | Schlinz |
| 2006/0087053 A1 | 4/2006 | O'Donnell et al. |
| 2006/0105075 A1 | 5/2006 | Otsubo |
| 2006/0189954 A1 | 8/2006 | Kudo et al. |
| 2006/0228969 A1 | 10/2006 | Erdman |
| 2006/0270302 A1 | 11/2006 | Ando et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0131335 A1 | 6/2007 | Zhou et al. |
| 2007/0141311 A1 | 6/2007 | Mleziva et al. |
| 2007/0179466 A1 | 8/2007 | Tremblay et al. |
| 2007/0196650 A1 * | 8/2007 | Yamamoto ............. D01F 1/10 |
| | | 428/375 |
| 2008/0134487 A1 | 6/2008 | Hartono |
| 2008/0149292 A1 | 6/2008 | Scherb |
| 2008/0161768 A1 | 7/2008 | Baba et al. |
| 2008/0287897 A1 | 11/2008 | Guzman et al. |
| 2009/0177176 A1 | 7/2009 | Saito |

(56) References Cited

U.S. PATENT DOCUMENTS

| | | |
|---|---|---|
| 2009/0204093 A1 | 8/2009 | Vasic |
| 2009/0312730 A1 | 12/2009 | LaVon et al. |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1 | 3/2010 | Hayase et al. |
| 2010/0248575 A1 | 9/2010 | Malz |
| 2010/0307668 A1 | 12/2010 | Lange et al. |
| 2011/0092943 A1 | 4/2011 | Bishop |
| 2011/0118689 A1 | 5/2011 | Een et al. |
| 2011/0120897 A1 | 5/2011 | Takahashi |
| 2011/0250378 A1 | 10/2011 | Eaton et al. |
| 2012/0004633 A1 | 1/2012 | Marcelo et al. |
| 2012/0061015 A1 | 3/2012 | LaVon et al. |
| 2012/0061016 A1 | 3/2012 | LaVon et al. |
| 2012/0071852 A1 | 3/2012 | Tsang et al. |
| 2012/0095429 A1 | 4/2012 | Kobayashi et al. |
| 2012/0271267 A1 | 10/2012 | Love |
| 2012/0277713 A1 | 11/2012 | Raycheck |
| 2012/0323206 A1 | 12/2012 | Mcmorrow |
| 2013/0032656 A1 | 2/2013 | Yamamoto et al. |
| 2013/0059494 A1* | 3/2013 | Tam .................. B32B 5/26 428/221 |
| 2013/0072887 A1 | 3/2013 | LaVon et al. |
| 2013/0102982 A1 | 4/2013 | Nakano |
| 2013/0112584 A1 | 5/2013 | Gaspari et al. |
| 2013/0139960 A1 | 6/2013 | Maruyama et al. |
| 2013/0171421 A1 | 7/2013 | Weisman et al. |
| 2013/0199696 A1 | 8/2013 | Schneider et al. |
| 2013/0199707 A1 | 8/2013 | Schneider |
| 2013/0211356 A1 | 8/2013 | Nishikawa et al. |
| 2013/0211363 A1 | 8/2013 | Lavon |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0261589 A1 | 10/2013 | Fujkawa et al. |
| 2013/0306226 A1 | 11/2013 | Zink et al. |
| 2014/0000794 A1 | 1/2014 | Hamilton et al. |
| 2014/0005621 A1 | 1/2014 | Roe |
| 2014/0018759 A1 | 1/2014 | Jayasinghe et al. |
| 2014/0041797 A1 | 2/2014 | Schneider |
| 2014/0107605 A1 | 4/2014 | Schroer, Jr |
| 2014/0127460 A1 | 5/2014 | Xu et al. |
| 2014/0136893 A1 | 5/2014 | Xie et al. |
| 2014/0148773 A1 | 5/2014 | Brown et al. |
| 2014/0234575 A1 | 8/2014 | Mitsuno |
| 2014/0235127 A1 | 8/2014 | DeJesus et al. |
| 2014/0257231 A1 | 9/2014 | Wang et al. |
| 2014/0276517 A1 | 9/2014 | Chester et al. |
| 2014/0288521 A1 | 9/2014 | Wade |
| 2014/0296815 A1 | 10/2014 | Takken et al. |
| 2014/0302286 A1 | 10/2014 | Okuda |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie et al. |
| 2015/0083309 A1 | 3/2015 | Long et al. |
| 2015/0126956 A1 | 5/2015 | Raycheck |
| 2015/0136893 A1 | 5/2015 | Koskol |
| 2015/0164708 A1 | 6/2015 | Hashimoto |
| 2015/0167207 A1* | 6/2015 | Bongartz ............. B65H 51/005 428/221 |
| 2015/0173967 A1 | 6/2015 | Kreuzer et al. |
| 2015/0230995 A1 | 8/2015 | Kaneko et al. |
| 2015/0245958 A1 | 9/2015 | Chmielewski |
| 2015/0257941 A1 | 9/2015 | Eckstein |
| 2015/0282999 A1 | 10/2015 | Arizti et al. |
| 2015/0320612 A1 | 11/2015 | Seitz |
| 2015/0320613 A1 | 11/2015 | Seitz et al. |
| 2015/0320619 A1 | 11/2015 | Seitz et al. |
| 2015/0320620 A1 | 11/2015 | Seitz |
| 2015/0320622 A1 | 11/2015 | Seitz |
| 2015/0328056 A1 | 11/2015 | Een et al. |
| 2015/0351972 A1 | 12/2015 | Bing-Wo |
| 2016/0058624 A1 | 3/2016 | Hohm |
| 2016/0058627 A1 | 3/2016 | Barnes et al. |
| 2016/0067119 A1 | 3/2016 | Weisman et al. |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman |
| 2016/0228305 A1 | 8/2016 | Gualtieri et al. |
| 2016/0270977 A1 | 9/2016 | Surushe et al. |
| 2016/0331600 A1 | 11/2016 | Polidori et al. |
| 2017/0014281 A1 | 1/2017 | Xie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0065461 A1 | 3/2017 | Schneider |
| 2017/0079852 A1 | 3/2017 | Fujima et al. |
| 2017/0119595 A1 | 5/2017 | Carla et al. |
| 2017/0191198 A1 | 7/2017 | Ashraf et al. |
| 2017/0258650 A1 | 9/2017 | Rosati et al. |
| 2017/0281417 A1 | 10/2017 | Ishikawa |
| 2017/0319403 A1 | 11/2017 | Bewick-Sonntag et al. |
| 2017/0348163 A1 | 12/2017 | Lakso et al. |
| 2018/0092784 A1 | 4/2018 | Wade et al. |
| 2018/0140473 A1 | 5/2018 | Koshijima |
| 2018/0168874 A1 | 6/2018 | LaVon et al. |
| 2018/0168875 A1 | 6/2018 | LaVon et al. |
| 2018/0168876 A1 | 6/2018 | LaVon et al. |
| 2018/0168877 A1 | 6/2018 | Schneider et al. |
| 2018/0168878 A1 | 6/2018 | Schneider et al. |
| 2018/0168879 A1 | 6/2018 | Schneider et al. |
| 2018/0168880 A1 | 6/2018 | Schneider et al. |
| 2018/0168885 A1 | 6/2018 | Zink, II et al. |
| 2018/0168887 A1 | 6/2018 | LaVon et al. |
| 2018/0168888 A1 | 6/2018 | Zink |
| 2018/0168889 A1 | 6/2018 | LaVon et al. |
| 2018/0168890 A1 | 6/2018 | LaVon et al. |
| 2018/0168891 A1 | 6/2018 | Wise et al. |
| 2018/0168892 A1 | 6/2018 | LaVon et al. |
| 2018/0168893 A1 | 6/2018 | Ashraf et al. |
| 2018/0169964 A1 | 6/2018 | Schneider et al. |
| 2018/0170026 A1 | 6/2018 | Schneider et al. |
| 2018/0170027 A1 | 6/2018 | Schneider et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf |
| 2018/0333311 A1 | 11/2018 | Maki |
| 2019/0003079 A1 | 1/2019 | Ashraf |
| 2019/0003080 A1 | 1/2019 | Ashraf |
| 2019/0070041 A1 | 3/2019 | Schneider et al. |
| 2019/0070042 A1 | 3/2019 | Beck |
| 2019/0112737 A1 | 4/2019 | Ashraf |
| 2019/0246196 A1 | 8/2019 | Han |
| 2019/0254881 A1 | 8/2019 | Ishikawa |
| 2019/0298586 A1 | 10/2019 | Ashraf |
| 2019/0298587 A1 | 10/2019 | Ashraf |
| 2019/0374392 A1 | 12/2019 | Ninomiya |
| 2019/0374404 A1 | 12/2019 | Ninomiya |
| 2020/0155370 A1 | 5/2020 | Ohtsubo |
| 2020/0155371 A1 | 5/2020 | Ohtsubo |
| 2020/0206040 A1 | 7/2020 | Andrews |
| 2020/0214901 A1 | 7/2020 | Andrews |
| 2020/0298545 A1 | 9/2020 | Andrews |

FOREIGN PATENT DOCUMENTS

| | | |
|---|---|---|
| CN | 1685099 | 10/2005 |
| CN | 101746057 A | 6/2010 |
| CN | 105997351 A | 10/2016 |
| EP | 0989218 A1 | 3/2000 |
| EP | 1305248 B1 | 5/2003 |
| EP | 1452157 A1 | 9/2004 |
| EP | 1473148 A1 | 11/2004 |

(56) References Cited

FOREIGN PATENT DOCUMENTS

| | | |
|---|---|---|
| EP | 1393701 B1 | 7/2013 |
| EP | EP 3 092 997 B1 | 8/2017 |
| EP | 3251642 A1 | 12/2017 |
| EP | 3257488 A1 | 12/2017 |
| EP | 3563817 A1 | 11/2019 |
| JP | H03213543 A | 9/1991 |
| JP | H0430847 A | 2/1992 |
| JP | H06254117 | 9/1994 |
| JP | H08071107 A | 3/1996 |
| JP | H08132576 | 5/1996 |
| JP | 2000026015 A | 1/2000 |
| JP | 2000160460 A | 6/2000 |
| JP | 3086141 B2 | 9/2000 |
| JP | 2002035029 A | 2/2002 |
| JP | 2002178428 A | 6/2002 |
| JP | 2002248127 A | 9/2002 |
| JP | 2003521949 A | 7/2003 |
| JP | 2004081365 A | 3/2004 |
| JP | 2004229857 A | 8/2004 |
| JP | 2004237410 A | 8/2004 |
| JP | 2004254862 A | 9/2004 |
| JP | 2004298362 A | 10/2004 |
| JP | 2005320636 A | 11/2005 |
| JP | 2006149747 A | 6/2006 |
| JP | 2006149749 A | 6/2006 |
| JP | 2006204673 A | 12/2006 |
| JP | 2007190397 A | 8/2007 |
| JP | 2008029749 A | 2/2008 |
| JP | 2008055198 A | 3/2008 |
| JP | 2008104853 A | 5/2008 |
| JP | 2008105425 A | 5/2008 |
| JP | 2008148942 A | 7/2008 |
| JP | 2008154998 A | 7/2008 |
| JP | 2008179128 A | 8/2008 |
| JP | 2008194493 A | 8/2008 |
| JP | 2008229006 A | 10/2008 |
| JP | 2008229007 A | 10/2008 |
| JP | 2008253290 | 10/2008 |
| JP | 2008260131 A | 10/2008 |
| JP | 2008264480 A | 11/2008 |
| JP | 2008272250 A | 11/2008 |
| JP | 2008272253 A | 11/2008 |
| JP | 2008296585 A | 12/2008 |
| JP | 2009000161 A | 1/2009 |
| JP | 2009039341 A | 2/2009 |
| JP | 2009056156 A | 3/2009 |
| JP | 2009106667 A | 5/2009 |
| JP | 2009172231 A | 8/2009 |
| JP | 2009240804 A | 10/2009 |
| JP | 2009241607 A | 10/2009 |
| JP | 2010131833 A | 6/2010 |
| JP | 2011015707 | 1/2011 |
| JP | 2011111165 A | 6/2011 |
| JP | 2011178124 A | 9/2011 |
| JP | 2011225000 A | 11/2011 |
| JP | 2012050882 A | 3/2012 |
| JP | 2012050883 A | 3/2012 |
| JP | 2012115358 A | 6/2012 |
| JP | 2012521498 A | 9/2012 |
| JP | 5124187 B2 | 11/2012 |
| JP | 5124188 B2 | 11/2012 |
| JP | 2013138795 A | 7/2013 |
| JP | 2014097257 | 5/2014 |
| JP | 2014111222 A | 6/2014 |
| JP | 2014188042 | 10/2014 |
| JP | 2015510831 A | 4/2015 |
| JP | 2015521499 A | 7/2015 |
| JP | 2016013687 A | 1/2016 |
| JP | 2016016536 A | 2/2016 |
| JP | 5942819 B2 | 6/2016 |
| JP | 2016193199 A | 11/2016 |
| JP | 6149635 B2 | 6/2017 |
| JP | 2019081304 A | 5/2019 |
| JP | 2019166804 A | 10/2019 |
| JP | 2019181807 A | 10/2019 |
| JP | 2020054741 A | 4/2020 |
| JP | 2020054742 A | 4/2020 |
| JP | 2020054744 A | 4/2020 |
| JP | 2020054745 A | 4/2020 |
| WO | 9925296 A1 | 5/1999 |
| WO | 03059603 A1 | 7/2003 |
| WO | WO2008123348 | 10/2008 |
| WO | WO2003015681 | 2/2013 |
| WO | WO2013084977 | 6/2013 |
| WO | WO2014084168 A1 | 6/2014 |
| WO | WO2014196669 | 11/2014 |
| WO | 2016047320 A1 | 3/2016 |
| WO | WO2016056092 A1 | 4/2016 |
| WO | WO2016056093 A1 | 4/2016 |
| WO | WO2016063346 A1 | 4/2016 |
| WO | WO2016067387 A1 | 5/2016 |
| WO | WO2016071981 A1 | 5/2016 |
| WO | WO2016075974 A1 | 5/2016 |
| WO | WO2016098416 A1 | 6/2016 |
| WO | WO2016104412 A1 | 6/2016 |
| WO | WO2016104422 A1 | 6/2016 |
| WO | WO2016158499 A1 | 10/2016 |
| WO | WO2016158746 A1 | 10/2016 |
| WO | WO2016208502 A1 | 12/2016 |
| WO | WO2016208513 A1 | 12/2016 |
| WO | WO2017105997 | 6/2017 |
| WO | 2018061288 A1 | 4/2018 |
| WO | 2018084145 A1 | 5/2018 |
| WO | 2018154680 A1 | 8/2018 |
| WO | 2018154682 A1 | 8/2018 |
| WO | 2018167836 A1 | 9/2018 |
| WO | 2019046363 A1 | 3/2019 |
| WO | 2019111203 A1 | 6/2019 |
| WO | 2019150802 A1 | 8/2019 |
| WO | 2020006996 A1 | 1/2020 |

OTHER PUBLICATIONS

All Office Actions, U.S. Appl. No. 15/831,448.
All Office Actions, U.S. Appl. No. 15/832,929.
All Office Actions, U.S. Appl. No. 15/833,057.
All Office Actions, U.S. Appl. No. 15/838,405.
All Office Actions, U.S. Appl. No. 15/839,896.
All Office Actions, U.S. Appl. No. 15/846,382.
All Office Actions, U.S. Appl. No. 16/115,617.
3D Nonwovens Developments for textured nonwovens; Detlef Frey; http://web.archive.org/web/20170919080326/https://www.reicofil.com/en/pages/3d_nonwovens, Sep. 19, 2017.
PCT International Search Report, PCT/US2017/064596, dated Mar. 12, 2018.
American Cancer Society—What Cancer Patients Their Families and Caregivers Need to Know About COVID 19—Is Impacting Our Patient Services, dated Mar. 31, 2020, pp. 1-3.
ASTM "Standard Tables of Body Measurements for Children Infant Size—Preemie to 24 Months", dated Mar. 30, 2020, pp. 1-6.
ASTM "Standard Tables of Body Measurements for Adult Females Misses Figure Type Size Range 00-20" dated May 12, pp. 1-7.

* cited by examiner

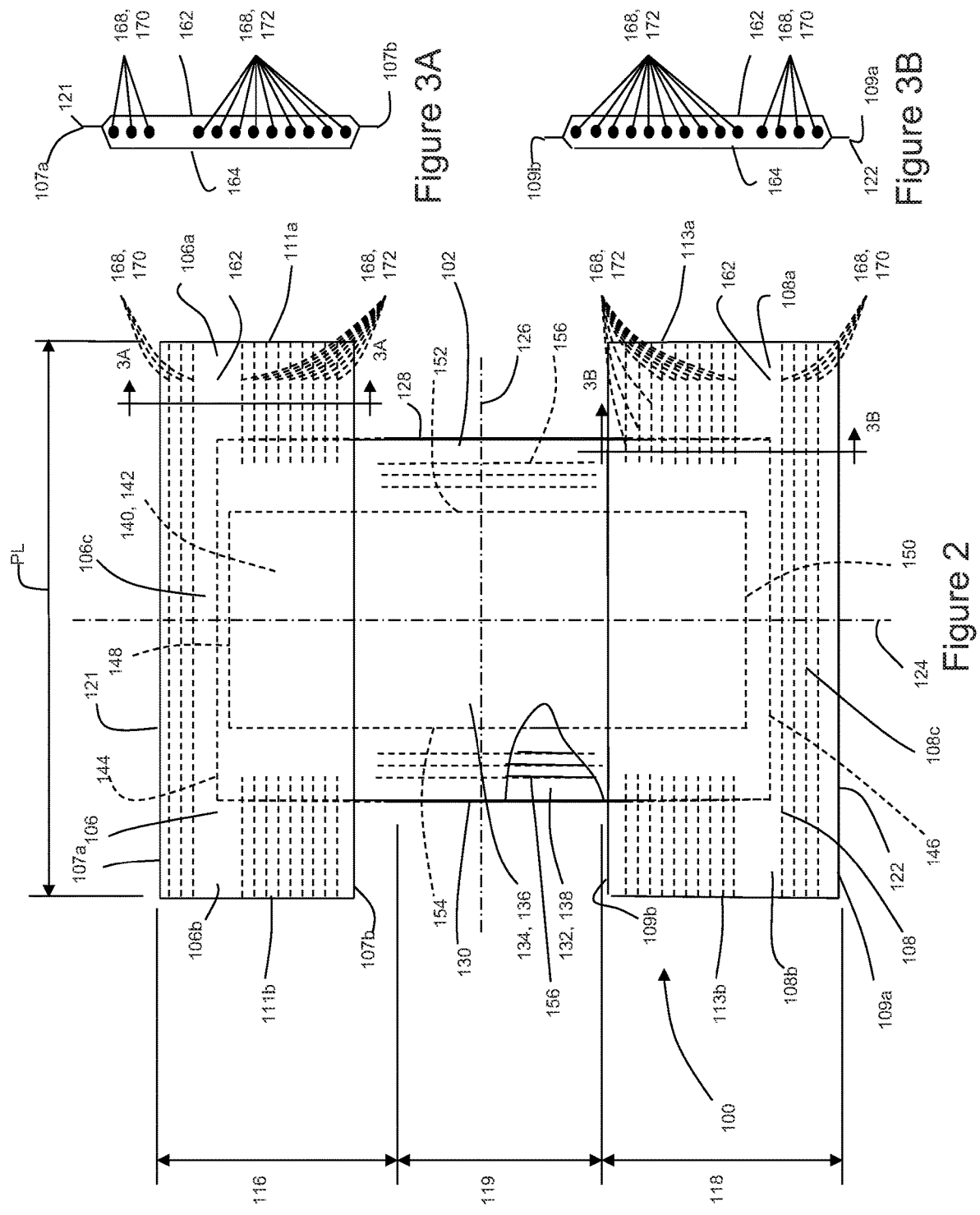

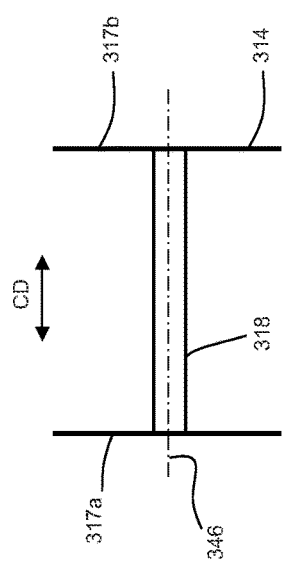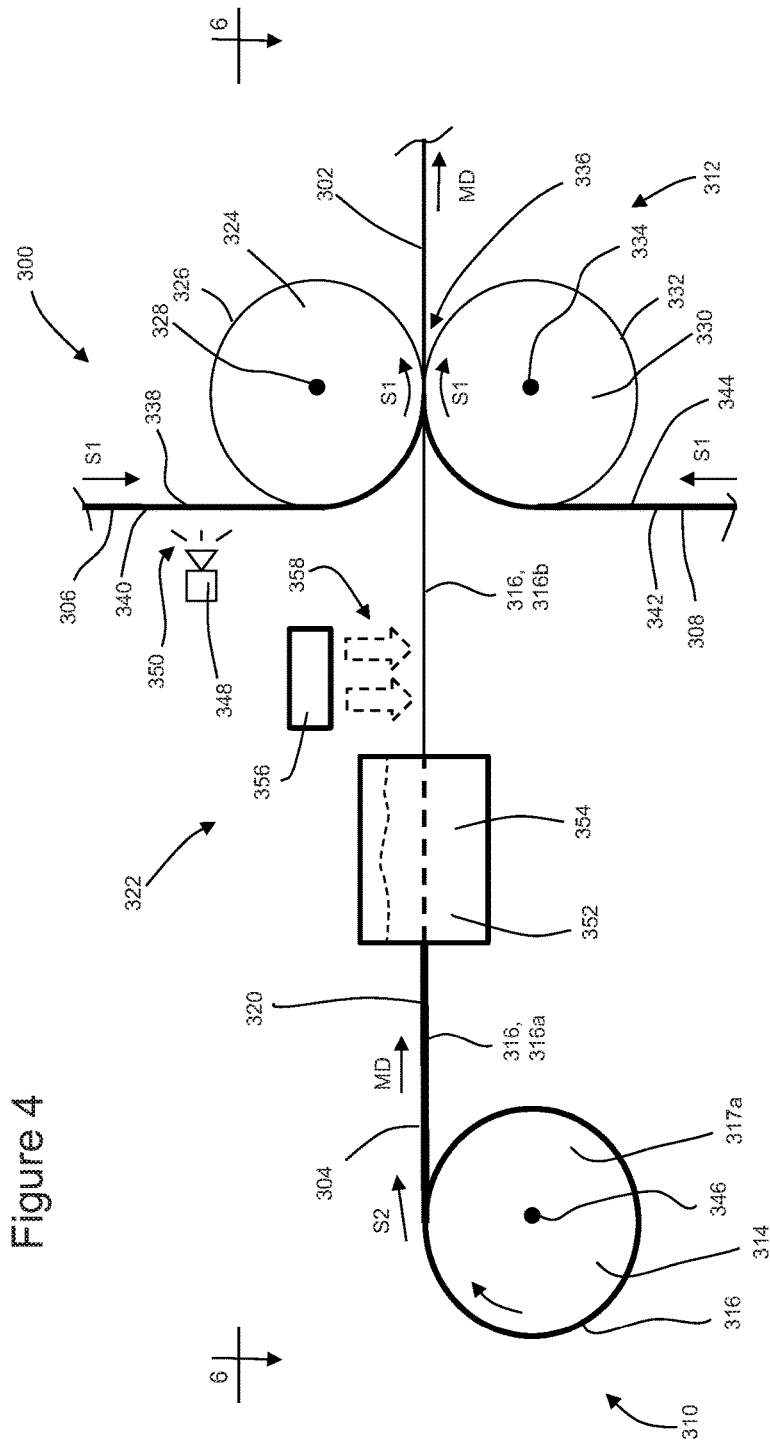

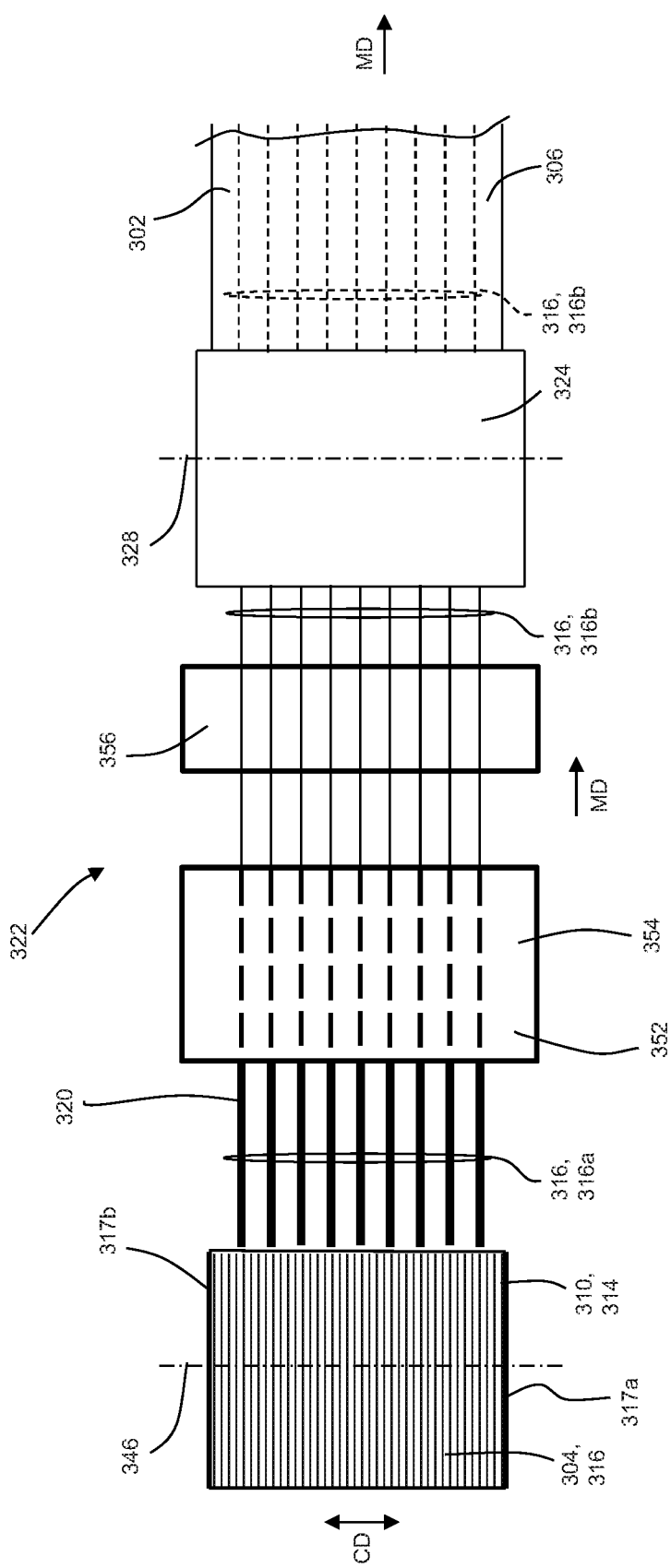

METHODS AND APPARATUSES FOR MAKING ELASTOMERIC LAMINATES WITH ELASTIC STRANDS PROVIDED WITH A SPIN FINISH

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands, and in turn, forms corrugations. The resulting elastomeric laminate is stretchable to the extent that the corrugations allow the elastic strands to elongate.

In some assembly processes, stretched elastic strands may be advanced in a machine direction and may be adhered between two advancing substrates, wherein the stretched elastic strands are spaced apart from each other in a cross direction. Some assembly processes are also configured with several elastic strands that are very closely spaced apart from each other in the cross direction. In some configurations, close cross directional spacing between elastic strands can be achieved by drawing elastic strands from windings that have been stacked in the cross direction on a beam. For example, various textile manufacturers may utilize beam elastics and associated handling equipment, such as available from Karl Mayer Corporation. However, problems can be encountered in manufacturing processes when drawing elastic strands stacked on a beam.

For example, relatively low decitex elastic strands supplied on a beam may include a coating, sometimes referred to a yarn finish or spin finish, to help prevent the elastics strands from adhering to themselves, each other, and/or downstream handling equipment. When constructing absorbent articles, hot melt adhesives are sometimes used to adhere stretched elastic stands to advancing substrates to create elastic laminates. However, hot melt adhesives used to adhere stretched elastic strands to substrates when constructing absorbent articles may not adhere well to strands having a spin finish. As such, increased amounts of adhesive may be required to adequately adhere the stretched elastic strands to the substrates than would otherwise be required for elastic stands without a spin finish. In turn, relatively larger amounts of adhesives required to bond the elastic strands to the substrates may have a negative impact on aspects of the resulting product, such as with respect to costs, functionality, and aesthetics.

Consequently, it would be beneficial to provide methods and apparatuses for producing elastomeric laminates by removing or substantially removing the spin finish from elastic strands unwound from beams before adhering the elastic strands to advancing substrates.

SUMMARY OF THE INVENTION

In one form, a method for making an elastomeric laminate comprises the steps of: providing an elastic strand wound onto a beam, wherein the elastic strand comprises a spin finish; rotating the beam to unwind the elastic strand from the beam; advancing the elastic strand from the rotating beam; removing a portion of the spin finish from the advancing elastic strand; stretching the elastic strand; and connecting the stretched elastic strand between a first substrate and a second substrate.

In another form, a method for making an elastomeric laminate comprises the steps of: providing a plurality of elastic strands wound onto a beam, wherein each elastic strand comprises a spin finish; rotating a first roller about a first axis of rotation extending in a cross direction, the first roller comprising an outer circumferential surface comprising a surface speed S1; providing a first substrate comprising a first surface and an opposing second surface; advancing the first surface of the first substrate onto the outer circumferential surface of the first roller; rotating the beam to unwind the plurality of elastic strands from the beam in a machine direction at a speed S2, wherein the plurality of elastic strands are separated from each other in the cross direction, and wherein S2 is less than S1; advancing the plurality of elastic strands from the beam in the machine direction; removing a portion of the spin finish from each of the advancing elastic strands; stretching the plurality of elastic strands in the machine direction by connecting the plurality of elastic strands with the second surface of the first substrate; and advancing the combined first substrate and the plurality of elastic strands from the first roller.

In yet another form, an apparatus for assembling an elastomeric laminate comprises: a means for advancing a first substrate; a beam comprising a plurality of elastic strands wound onto the beam, wherein each elastic strand comprises a spin finish; a means for applying detergent to remove a portion of the spin finish from each of the plurality of elastic strands; a means for stretching the plurality of elastic strands; and a means for connecting the stretched elastic strands with the first substrate.

BRIEF DESCRIPTION OF THE DRAWINGS

FIG. 2 is a partially cut away plan view of the diaper pant shown in FIGS. 1A and 1B in a flat, uncontracted state.

FIG. 3A is a cross-sectional view of the diaper pant of FIG. 2 taken along line 3A-3A.

FIG. 3B is a cross-sectional view of the diaper pant of FIG. 2 taken along line 3B-3B.

FIG. 4 shows an example of an empty beam having two side plates connected with opposing end portions of a mandrel core.

FIG. 5 is a schematic side view of a converting apparatus including a detergent bath adapted to remove a spin finish from a plurality of elastic strands before being adhered between a first substrate and a second substrate.

FIG. 6 is a view of the converting apparatus of FIG. 5 taken along line 6-6.

DETAILED DESCRIPTION OF THE INVENTION

Figure 1A:
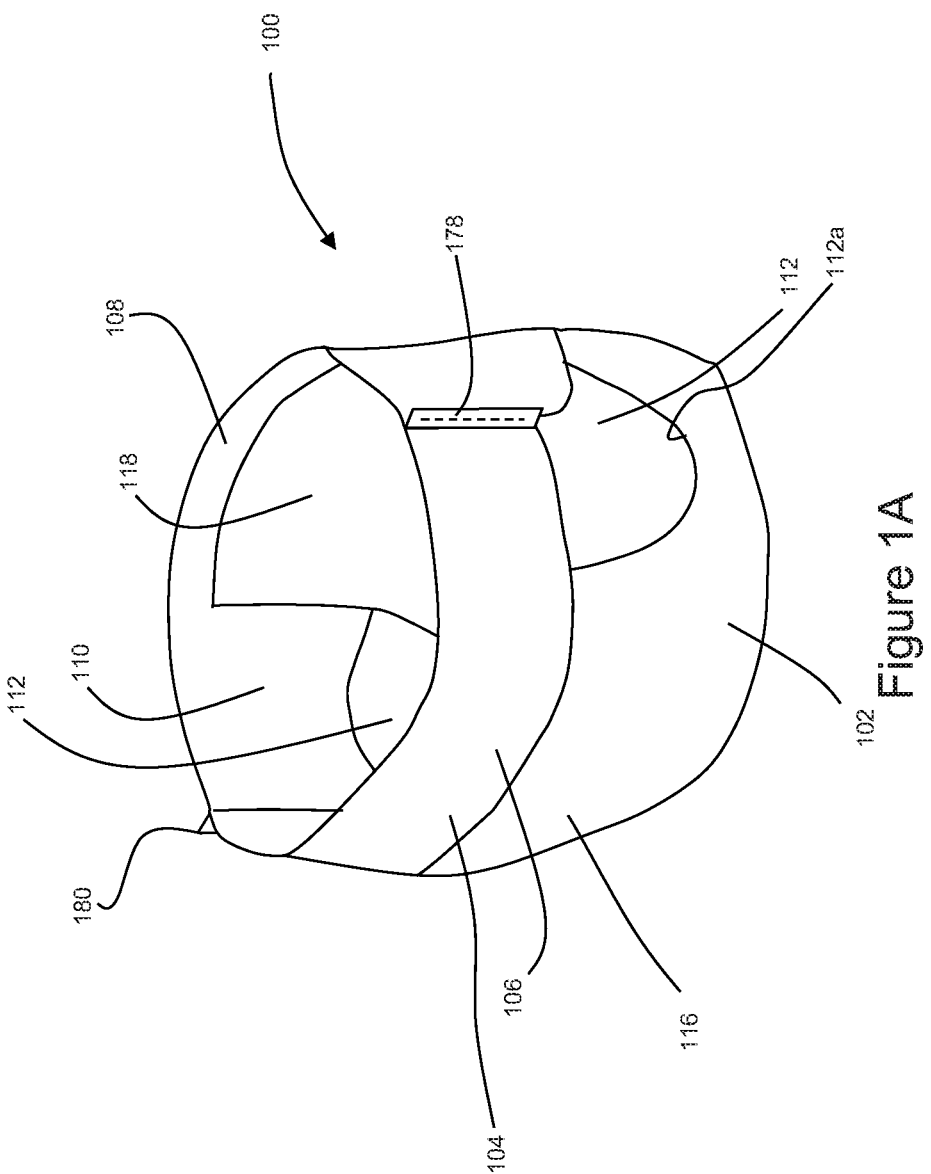
FIG. 1A is a front perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations in U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764

A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The present disclosure relates to methods for manufacturing absorbent articles, and in particular, to methods for making elastomeric laminates that may be used as components of absorbent articles. The elastomeric laminates may include a first substrate, a second substrate, and an elastic material located between the first substrate and second substrate. During the process of making the elastomeric laminate, the elastic material may be advanced and stretched in a machine direction and may be joined with either or both the first and second substrates advancing in the machine direction. The methods and apparatuses according to the present disclosure may be configured with a plurality of elastic strands wound onto a beam, wherein one or more elastic strands comprises a spin finish. During assembly of an elastomeric laminate, the beam is rotated to unwind the elastic strands from the beam. The elastic strands may be stretched while advancing in a machine direction. A portion of the spin finish may be removed from the advancing elastic strand with a spin finish removal apparatus. As discussed below, the spin finish removal apparatus may treat the advancing elastic strand to remove some or all the spin finish from the elastic strand. The spin finish removal apparatus may be configured to apply detergent to an advancing elastic strand and may also wipe and/or dry the advancing elastic strand. The treated stretched elastic strand may then be connected between a first substrate and a second substrate. In some configurations, adhesive may be applied to the treated the elastic strand, the first substrate, and/or the second substrate. As such, the methods and apparatuses are adapted to utilize elastic strands having a spin finish that are unwound from beams to produce elastomeric laminates. By removing the spin finish from the elastics strands, relatively less adhesive may be utilized to adhere the strands between the substrates.

As previously mentioned, the elastomeric laminates made according to the processes and apparatuses discussed herein may be used to construct various types of components used in the manufacture of different types of absorbent articles, such as diaper pants and taped diapers. To help provide additional context to the subsequent discussion of the process embodiments, the following provides a general description of absorbent articles in the form of diapers that include components including the elastomeric laminates that may be produced with the methods and apparatuses disclosed herein.

Figure 1B:
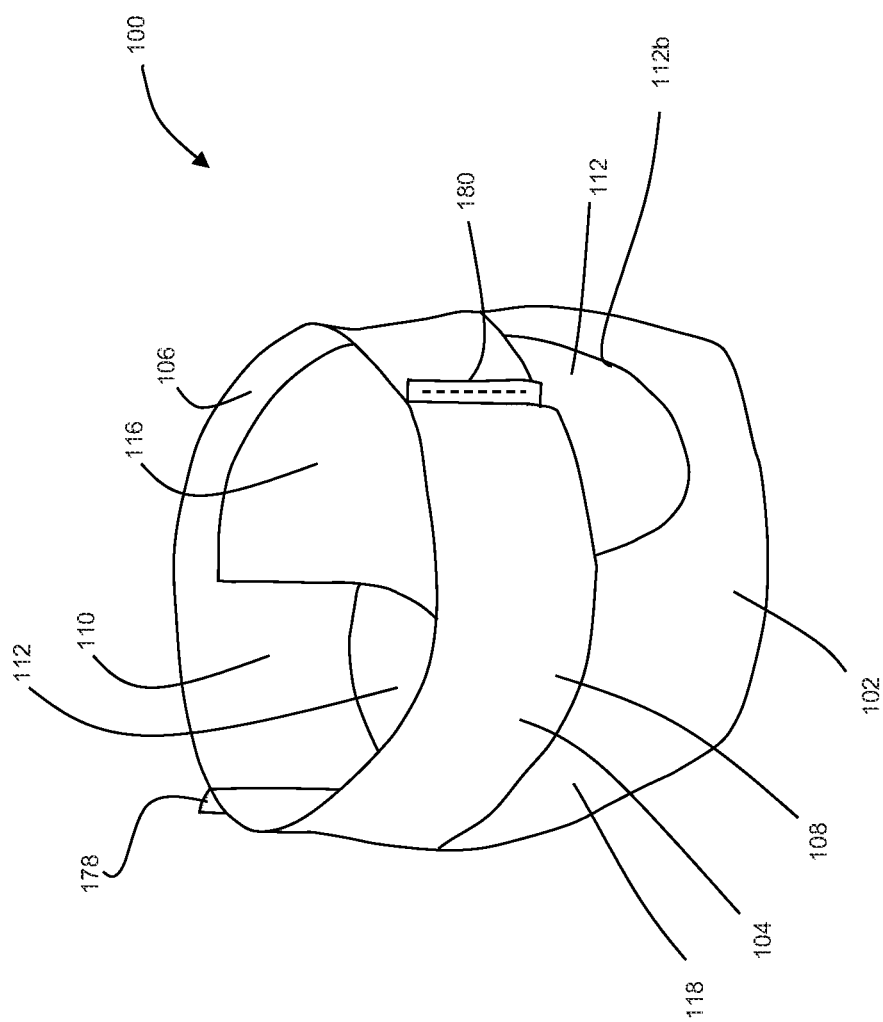
FIG. 1B is a rear perspective view of a diaper pant.

FIGS. 1A, 1B, and 2 show an example of a diaper pant 100 that may include components constructed from elastomeric laminates assembled in accordance with the apparatuses and methods disclosed herein. In particular, FIGS. 1A and 1B show perspective views of a diaper pant 100 in a pre-fastened configuration, and FIG. 2 shows a plan view of the diaper pant 100 with the portion of the diaper that faces away from a wearer oriented toward the viewer. The diaper pant 100 includes a chassis 102 and a ring-like elastic belt 104. As discussed below in more detail, a first elastic belt 106 and a second elastic belt 108 are bonded together to form the ring-like elastic belt 104.

With continued reference to FIG. 2, the diaper pant 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100 may include a backsheet 136. The backsheet 136 may also define the outer surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100 may include a topsheet 138. The topsheet 138 may also define all or part of the inner surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIG. 2, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 118 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As previously mentioned, apparatuses and methods according to the present disclosure may be utilized to produce elastomeric laminates that may be used to construct various components of diapers, such as elastic belts, leg cuffs, and the like. For example, FIGS. 4-11 show schematic views of converting apparatuses 300 adapted to manufacture elastomeric laminates 302. As described in more detail below, the converting apparatuses 300 shown in FIGS. 4-11 operate to advance a continuous length of elastic material 304, a continuous length of a first substrate 306, and a continuous length of a second substrate 308 along a machine direction MD. It is also to be appreciated that in some configurations, the first substrate and second substrate 306, 308 herein may be defined by two discrete substrates or may be defined by folded portions of a single substrate. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films.

The elastomeric laminates 302 can be used to construct various types of diaper components. For example, the elastomeric laminates 302 may be used as a continuous length of elastomeric belt material that may be converted into the first and second elastic belts 106, 108 discussed above with reference to FIGS. 1-3B. As such, the elastic material 304 may correspond with the belt elastic material 168 interposed between the outer layer 162 and the inner layer 164, which in turn, may correspond with either the first and/or second substrates 306, 308. In other examples, the elastomeric laminates may be used to construct waistbands and/or side panels in taped diaper configurations. In yet other examples, the elastomeric laminates may be used to construct various types of leg cuff and/or topsheet configurations.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, a metering device may comprise a beam of elastic strands wound thereon. During operation, elastic material may advance in a machine direction from a rotating beam to a downstream metering device to be joined with one or more advancing substrates. The elastic material advancing from the rotating beam may include a spin finish, and as such, the apparatuses herein may be configured to remove some or all the spin finish before joining the elastic material with the substrates. It is to be appreciated that the apparatuses and methods of assembly of elastomeric laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

As shown in FIGS. 4-6, a converting apparatus 300 for producing an elastomeric laminate 302 may include a first metering device 310 and a second metering device 312. The first metering device may be configured as a beam 314 with a plurality of elastic strands 316 wound thereon. FIG. 4 shows an example of an empty beam 314 that includes two side plates 317a, 317b that may be connected with opposing end portions of a mandrel core 318, wherein elastic strands may be wound onto the mandrel core 318. It is to be appreciated that beams of various sizes and technical specifications may be utilized in accordance with the methods and apparatuses herein, such as for example, beams that are available from ALUCOLOR Textilmaschinen, GmbH. During operation, the plurality of elastic strands 316 advance in the machine direction MD from the beam 314 to the second metering device 312. In addition, the plurality of elastic strands 316 may be stretched along the machine direction MD between the beam 314 and the second metering device 312. The stretched elastic strands 316 are also joined with a first substrate 306 and a second substrate 308 at the second metering device 312 to produce an elastomeric laminate 302. As discussed in more detail below, one or more of the elastic strands 316a advancing from the beam 314 may include a spin finish 320 located on outer surfaces of the elastics strands. In turn, all or some of the spin finish 320 may be removed from the advancing elastic strands 316a with a spin finish removal apparatus 322. In turn, treated stretched elastic strands 316b may then be connected between the first substrate 306 and the second substrate 308.

It is to be appreciated the elastic strands 316 may include various types of spin finish 320, also referred herein as yarn finish, configured as coating on the elastic strands 316 that may be intended to help prevent the elastics strands from adhering to themselves, each other, and/or downstream handling equipment. In some configurations, a spin finish may include various types of oils and other components, such as disclosed for example in U.S. Pat. Nos. 8,377,554; 8,093,161; and 6,821,301. In some configurations, a spin finish may include various types of silicone oils, such as for example, polydimethylsiloxane. In some configurations, a spin finish may include various types of mineral oils.

As shown in FIGS. 5 and 6, the second metering device 312 may include: a first roller 324 having an outer circumferential surface 326 and that rotates about a first axis of rotation 328, and a second roller 330 having an outer circumferential surface 332 and that rotates about a second axis of rotation 334. The first roller 324 and the second roller 330 rotate in opposite directions, and the first roller 324 is adjacent the second roller 330 to define a nip 336 between the first roller 324 and the second roller 330. The first roller 324 rotates such that the outer circumferential surface 326 has a surface speed S1, and the second roller 330 may rotate such that the outer circumferential surface 332 has the same, or substantially the same, surface speed S1.

With continued reference to FIGS. 5 and 6, the first substrate 306 includes a first surface 338 and an opposing second surface 340, and the first substrate 306 advances to the first roller 324. In particular, the first substrate 306 advances at speed S1 to the first roller 324 where the first substrate 306 partially wraps around the outer circumferential surface 326 of the first roller 324 and advances through the nip 336. As such, the first surface 338 of the first substrate 306 travels in the same direction as and in contact with the outer circumferential surface 326 of the first roller 324. In addition, the second substrate 308 includes a first surface 342 and an opposing second surface 344, and the second substrate 308 advances to the second roller 330. In particular, the second substrate 308 advances at speed S1 to the second roller 330 where the second substrate 308 partially wraps around the outer circumferential surface 332 of the second roller 330 and advances through the nip 336. As such, the second surface 344 of the second substrate 308 travels in the same direction as and in contact with the outer circumferential surface 332 of the second roller 330.

Still referring to FIGS. 5 and 6, the beam 314 includes elastic strands 316 wound thereon, and the beam 314 is rotatable about a beam rotation axis 346. In some configurations, the beam rotation axis 346 may extend in the cross direction CD. As the beam 314 rotates, the elastic strands 316 advance from the beam 314 at a speed S2 with the elastic strands 316 being spaced apart from each other in the cross direction CD. From the beam 314, the elastic strands 316 advance in the machine direction MD to the nip 336. In some configurations, the speed S2 is less than the speed S1, and as such, the elastic strands 316 are stretched in the machine direction MD. In turn, the stretched elastic strands 316 advance through the nip 336 between the first and second substrates 306, 308 such that the elastic strands 316 are joined with the second surface 340 of the first substrate 306 and the first surface 342 of the second substrate 308 to produce a continuous length of elastomeric laminate 302.

As discussed above, one or more of the elastic strands 316*a* advancing from the beam 314 may include a spin finish 320. In turn, the advancing elastic strands 316*a* may be treated with the spin finish removal apparatus 322 that may remove some or all the spin finish 320. As such, the treated elastic strands 316*b* having some or all the spin finish 320 removed may advance from the spin finish removal apparatus 322 to be joined with the first substrate 306 and the second substrate 308 to form the elastomeric laminate 302.

As shown in FIG. 5, the first substrate 306 may advance past an adhesive applicator device 348 that applies adhesive 350 to the second surface 340 of the first substrate 306 before advancing to the nip 336. It is to be appreciated that the adhesive 350 may be applied to the first substrate 306 upstream of the first roller 324 and/or while the first substrate 306 is partially wrapped around the outer circumferential surface 326 of the first roller 324. It is to be appreciated that adhesive may be applied to the treated elastic strands 316*b* before and/or while being joined with first substrate 306 and second substrate 308. In addition, it is to be appreciated that adhesive may be applied to the first surface 342 of the second substrate 308 before or while being joined with the treated elastic strands 316*b* and the first substrate 306.

As shown in FIGS. 5 and 6, the spin finish removal apparatus 322 may be configured to include a bath 352 containing a detergent 354. As such the elastic strands 316*a* having a spin finish 320 advance from the beam 314 to the bath 352, wherein the elastic strands 316*a* advance through the detergent 354 adapted to remove some or all the spin finish 320 from the elastic strands 316. As shown in FIGS. 5 and 6, the spin finish removal apparatus 322 may also be configured to include a drying apparatus 356 to remove the detergent 354 from the elastic strands 316. It is to be appreciated that the drying apparatus 356 may be configured in various ways, such as a fan, a blower, a heater, and/or combinations thereof. In some configurations, the drying apparatus 356 may move air or some other gas 358 relative to the elastic strands 316 to evaporate the detergent from the elastic strands 316. As such, the treated elastic strands 316*b* may advance from the bath 352 to the drying apparatus 356 to remove some or all the detergent from the treated elastic strands 316*b*. In turn, the treated elastic strands 316*b* may advance from the drying apparatus 356 to be combined with the first substrate 306 and the second substrate 308.

It is to be appreciated that various configurations of detergent 354 may be used to remove spin finish 320 from the elastic strands 316. For example, in some configurations, a detergent may include various different ingredients, such as those included for example in TISSOCYL RC available from Zschimmer & Schwarz GmbH.

It is to be appreciated that different components may be used to construct the elastomeric laminates 302 in accordance with the methods and apparatuses herein. For example, the first and/or second substrates 306, 308 may include nonwovens and/or films. In addition, the elastic strands 316 may be configured in various ways and having various decitex values. In some configurations, the elastic strands 316 may be configured with decitex values ranging from about 10 decitex to about 500 decitex, specifically reciting all 1 decitex increments within the above-recited range and all ranges formed therein or thereby. It is also to be appreciated the beam 314 may be configured in various ways and with various quantities of elastic strands. Example beams, also referred to as warp beams, that may be used with the apparatus and methods herein are disclosed in U.S. Pat. Nos. 4,525,905; 5,060,881; and 5,775,380; and U.S. Patent Publication No. 2004/0219854 A1. Although FIG. 6 shows nine elastic strands 316 advancing from the beam 314, it is to be appreciated that the apparatuses herein may be configured such that more or less than nine elastic strands 316 advance from the beam 314. In some configurations, the elastic strands 316 advancing from the beam 314 may include from about 100 to about 2000 strands, specifically reciting all 1 strand increments within the above-recited range and all ranges formed therein or thereby. In some configurations, the elastic strands 316 may be separated from each other by about 0.5 mm to about 4 mm in the cross direction, specifically reciting all 0.1 mm increments within the above-recited range and all ranges formed therein or thereby. As discussed herein, the elastics in the plurality of elastic strands may be pre-strained prior to joining the elastic strand to the first or second substrate layers 306, 308. In some configurations, the elastic may be pre-strained from about 75% to about 300%, specifically reciting all 1% increments within the above-recited range and all ranges formed therein or thereby. It is also to be appreciated that one or more beams of elastics may be arranged along the cross direction CD of a converting process and/or arranged along a machine direction MD in various different portions of a converting process. It is also to be appreciated that the beam 314 can be connected with one or more motors, such as servo motors, to drive and control the rotation of the beam 314.

It is to be appreciated that the apparatuses 300 herein may be configured in various ways with various features described herein to assemble elastomeric laminates 302 having various stretch characteristics. For example, the apparatus 300 may be configured to assemble elastomeric laminates 302 with elastic strands 316 unwound from more than one beam and/or in combination with elastic stands supplied from an overend unwinder. The elastic strands may be joined with the first and second substrates 306, 308 such that the elastomeric laminate 302 may have different stretch characteristics in different regions along the cross direction CD. For example, when the elastomeric laminate 302 is elongated, some elastic strands may exert contraction forces in the machine direction MD that are different from contraction forces exerted by other elastic strands. Such differential stretch characteristics can be achieved by stretching some elastic strands more or less than other elastic strands before joining the elastic strands with the first and second substrates 306, 308. It is also to be appreciated that the elastic strands may have various different material constructions and/or decitex values to create elastomeric laminates 302 having different stretch characteristics in different regions. In some configurations, the elastomeric laminate may have regions where the elastic strands are spaced relatively close to one another in the cross direction CD and other regions where the elastic strands are spaced relatively farther apart from each other in the cross direction CD to create different stretch characteristics in different regions. In some configurations, the elastic strands may be supplied on the beam in a stretched state, and as such, may not require additional stretching (or may require relatively less additional stretching) before being combined with the first substrate 306 and/or the second substrate 308.

Figure 7:
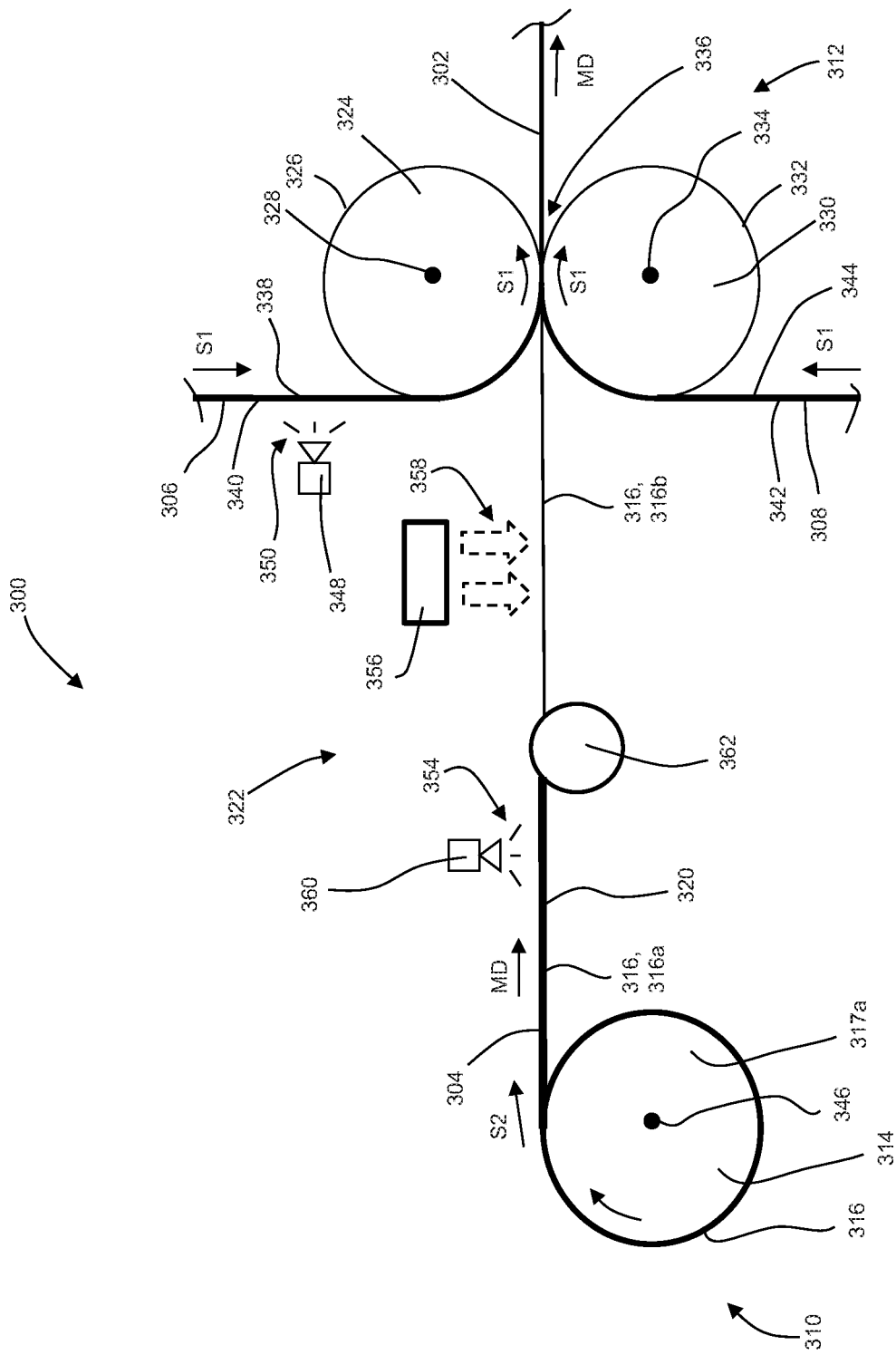
FIG. 7 is a schematic side view of a converting apparatus including a detergent spray and wiper adapted to remove a spin finish from a plurality of elastic strands before being adhered between a first substrate and a second substrate.

It is to be appreciated that the spin finish removal apparatus 322 may be configured in various ways. For example as shown in FIG. 7, the spin finish removal apparatus 322 may include one or more detergent applicator devices 360, such as a nozzle, that sprays detergent 354 onto the spin finish 320 of advancing elastic strands 316a. With continued reference to FIG. 7, the spin finish removal apparatus 322 may also include a wiper 362 downstream of the detergent applicator device 360 that is configured to wipe detergent 354 and/or spin finish 320 from the elastic strands 316. The elastic strands 316 may then advance from the wiper 362 to the drying apparatus 356 such as described above. It is to be appreciated that the wiper 362 may be in direct contact with the elastic strands and may be configured as a static device or may be configured to move relative to the elastic strands 316. For example, the wiper 362 may be configured with an outer surface in contact with the elastic strands 316 that rotates in a direction opposite of the machine direction MD of the advancing elastic strands 316. In some configurations, the wiper 362 may be configured with an outer surface in contact with the elastic strands 316 that rotates in a same direction as the machine direction MD of the advancing elastic strands 316 wherein the outer surface may move faster or slower than the speed of the elastic strands 316.

Figure 8:
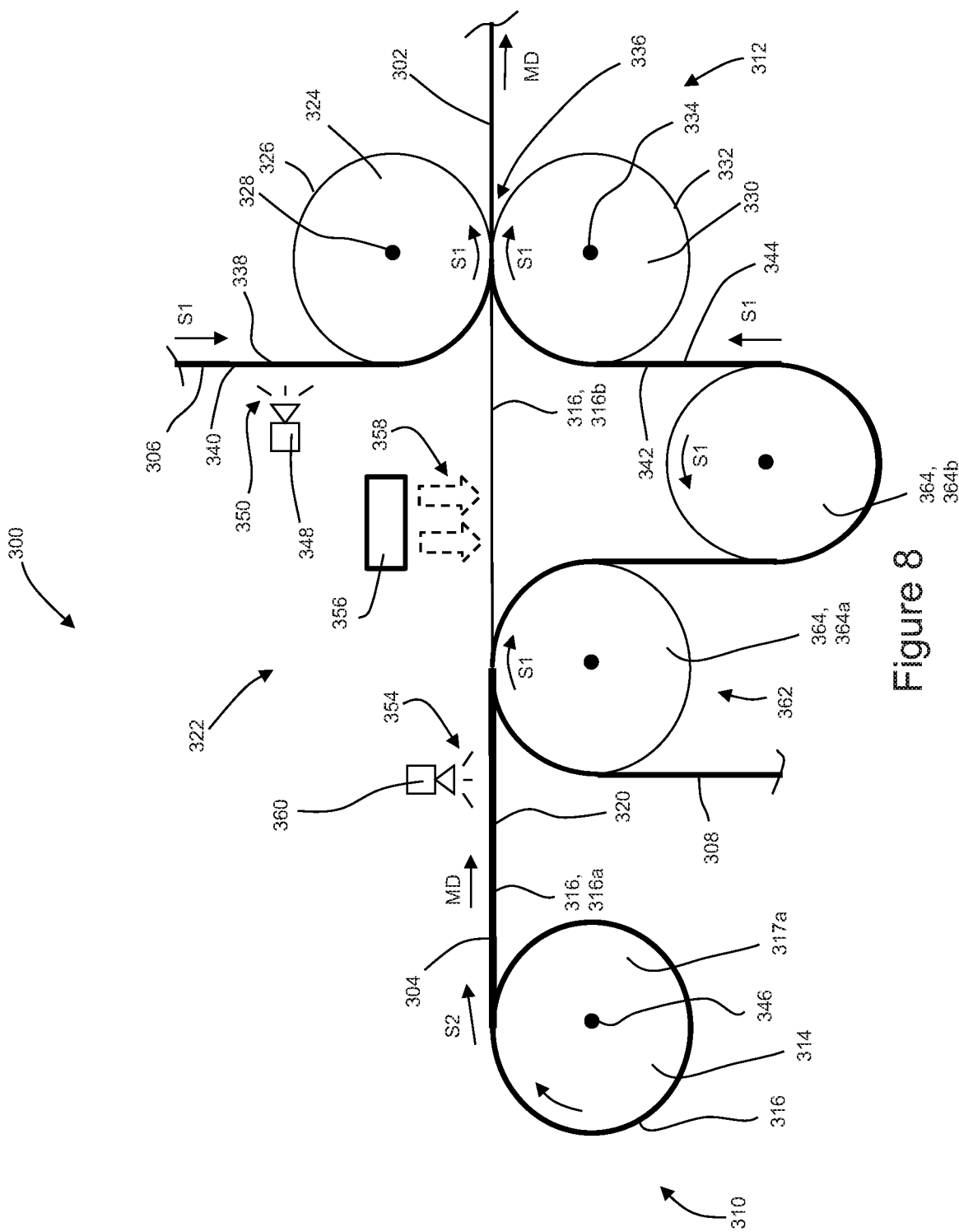
FIG. 8 is a schematic side view of a converting apparatus wherein a first substrate is configured to wipe a spin finish from a plurality of elastic strands before being adhered between the first substrate and a second substrate.

In some configurations, the first and/or second substrates 306, 308 may be used in conjunction with a wiper 362 to remove detergent 354 and/or spin finish 320 from the elastic strands 316. For example, FIG. 8 shows a configuration wherein the advancement path of second substrate 308 is configured such that the second substrate 308 contacts the elastic strands 316 to remove detergent 354 and/or spin finish 320. As shown in FIG. 8, the spin finish removal apparatus 322 may include one or more rotating drums 364 arranged such that before the second substrate 308 is combined with the elastic strands 316 and the first substrate 306, the second substrate 308 contacts the elastic strands 316. For example, the second substrate 308 may advance onto a first drum 364a wherein the second substrate 308 advances at a first speed S1. The first drum 364a rotates and brings first surface 342 of the second substrate 308 into contact with the elastic strands 316 advancing at a second speed S2, wherein S1 is not equal S2. As such, the second substrate 308 and the elastic strands 316 move relative to each other when in contact. In turn, the relative movement between the second substrate 308 and the elastic strands 316 may wipe detergent 354 and/or spin finish 320 from the elastic strands 316. From the first drum 364a, the second substrate 308 may advance to a second drum 364b before being combined with the elastic strands 316 and the first substrate 306 to form the elastomeric laminate 302.

It is to be appreciated that the advancement path of either or both the first substrate 306 and the second substrate 308 may be configured such that either or both the first substrate 306 and the second substrate 308 may advance and contact to the elastic strands 316 to wipe detergent 354 and/or spin finish 320 from the elastic strands 316. It is also to be appreciated that that the first surface 338 and/or the second surface 340 of the first substrate 306 and/or the first surface 342 and/or the second surface 344 of the second substrate 308 may be used to contact the elastic strands 316 and wipe detergent 354 and/or spin finish 320 from the elastic strands 316. In some configurations, the advancement path of the assembled elastic laminate 302 may be configured such that the either or both the first substrate 306 and the second substrate 308 of the elastic laminate 302 may contact the elastic strands 316 and wipe detergent 354 and/or spin finish 320 from the elastic strands 316 before the elastic strands 316 are joined with the first substrate 306 and the second substrate 308. In some configurations, the spin finish 320 and/or detergent 354 may be wiped onto one surface of either or both the first and second substrates 306, 308 and wherein the elastic strands 316 are bonded to the opposing surface of either or both the first and second substrates 306, 308 to help improve adhesion of the elastic strands 316 to the first substrate 306 and/or the second substrate 308.

Figure 9:
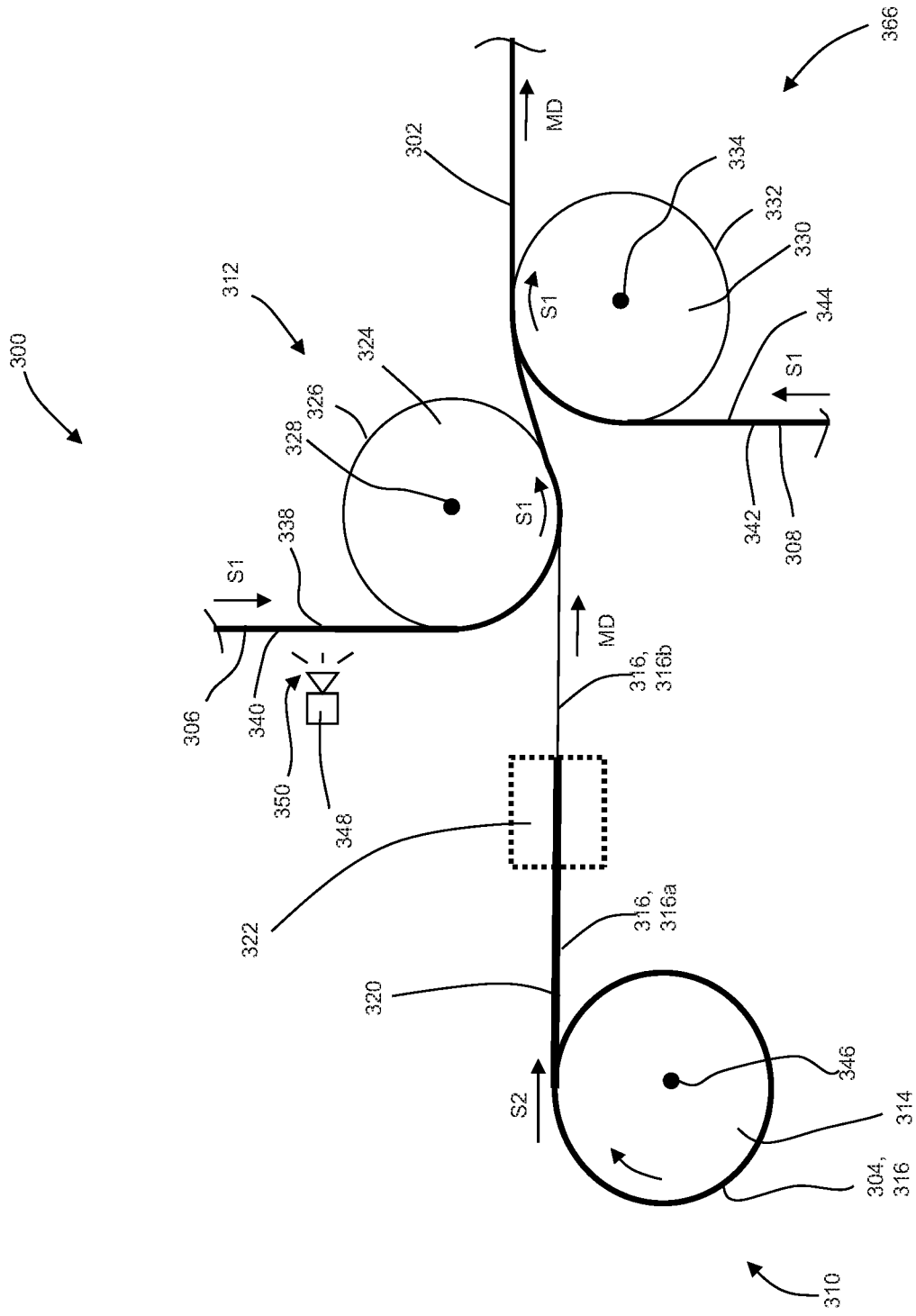
FIG. 9 is a schematic side view of a second configuration of a converting apparatus adapted to manufacture an elastomeric laminate including a spin finish removal apparatus.

It is to be appreciated that the apparatuses 300 herein may be configured in various ways with various features of the spin finish removal apparatuses 322 described herein to assemble elastomeric laminates 302. For example, in a second configuration of the apparatus 300 shown in FIG. 9, the second roller 330 may be positioned downstream from the first roller 324. As such, the first roller 324 may be configured as the second metering device 312 and the second roller 330 may be configured as a third metering device 366. As shown in FIG. 9, the first substrate 306 advances at speed S1 to the first roller 324 where the first substrate 306 partially wraps around the outer circumferential surface 326 of the first roller 324 and advances from the first roller to the second roller 330 to be combined with second substrate 308. As the beam 314 rotates, the elastic strands 316 advance from the beam 314 at a speed S2 with the elastic strands 316 being spaced apart from each other in the cross direction CD. From the beam 314, elastic strands 316a having a spin finish 320 advance to a spin finish removal apparatus 322 generically illustrated by a dashed-line rectangle. It is to be appreciated that the spin finish removal apparatus 322 may be configured with various combinations of features of the spin finish removal apparatus 322 described herein. In turn, all or some of the spin finish 320 may be removed from the advancing elastic strands 316a with the spin finish removal apparatus 322. As such, the treated elastic strands 316b having some or all the spin finish 320 removed may advance from the spin finish removal apparatus 322 to the first roller 324 and are positioned on the second surface 340 of the first substrate 306. In some configurations, the speed S2 is less than the speed S1, and as such, the elastic strands 316 are stretched in the machine direction MD.

With continued reference to FIG. 9, the first substrate 306 and the elastic strands 316 advance from the outer circumferential surface 326 of the first roller 324 to the second roller 330. In addition, the second substrate 308 advances at speed S1 to the second roller 330 where the second substrate 308 partially wraps around the outer circumferential surface 332 of the second roller 330. In turn, the combined first substrate 306 and the stretched elastic strands 316, 316b advance from first roller 324 to the second roller 330 and are combined with the second substrate 308 such that the elastic strands 316, 316b are joined with the second surface 340 of the first substrate 306 and the first surface 342 of the second substrate 308 to produce a continuous length of elastomeric laminate 302. As discussed above, the first substrate 306 may advance past an adhesive applicator device 348 that applies adhesive 350 to the second surface 340 of the first substrate 306 while advancing to the first roller 324. It is to be appreciated that the adhesive 350 may be applied to the first substrate 306 while the first substrate 306 is partially wrapped around the outer circumferential surface 326 of the first roller 324. It is to be appreciated that adhesive may also be applied to the elastic strands 316, 316b before and/or while being joined with first substrate 306 and second substrate 308. In addition, it is to be appreciated that adhesive may be applied to the first surface 342 of the second substrate 308 before or while being joined with the elastic strands 316 and first substrate 306.

Figure 10:
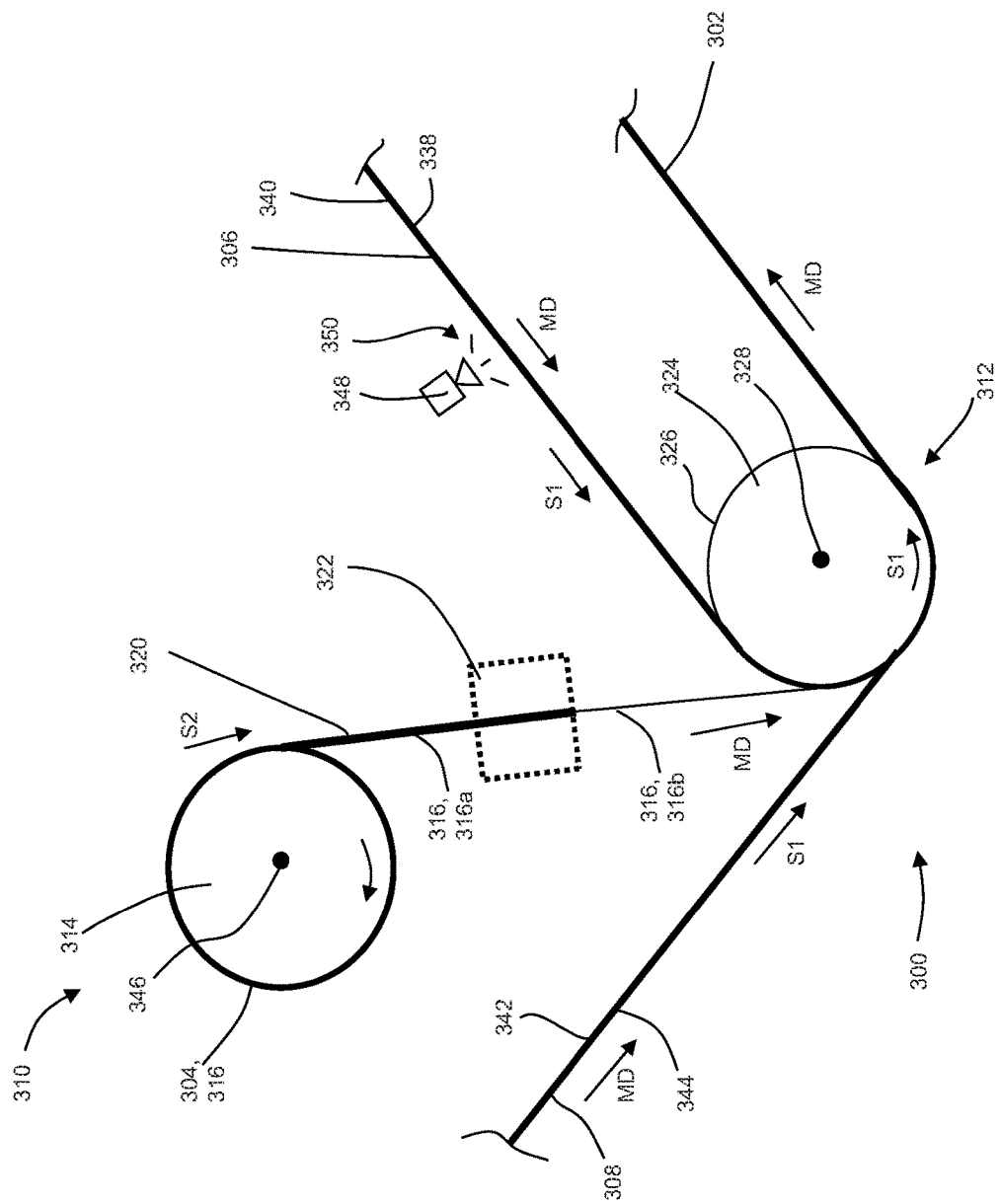
FIG. 10 is a schematic side view of a third configuration of a converting apparatus adapted to manufacture an elastomeric laminate including a spin finish removal apparatus.

In another configuration shown in FIG. 10, the apparatus 300 may be configured with only the first roller 324 and without a second roller 330. As such, the first roller 324 may be configured as the second metering device 312. As shown in FIG. 10, the first substrate 306 advances at speed S1 to the first roller 324 where the first substrate 306 partially wraps around the outer circumferential surface 326 of the first roller 324. While partially wrapped around the outer circumferential surface 326 of the first roller 324, the first substrate 306 is combined with the elastic strands 316, 316b and the second substrate 308. As the beam 314 rotates, the elastic strands 316 advance from the beam 314 at a speed S2 with the elastic strands 316 being spaced apart from each other in the cross direction CD. From the beam 314, elastic strands 316a having a spin finish 320 advance to a spin finish removal apparatus 322 generically illustrated by a dashed-line rectangle. As discussed above, it is to be appreciated that the spin finish removal apparatus 322 may be configured with various combinations of features of the spin finish removal apparatus 322 described herein. In turn, all or some of the spin finish 320 may be removed from the advancing elastic strands 316a with the spin finish removal apparatus 322. As such, the treated elastic strands 316b having some or all the spin finish 320 removed may advance from the spin finish removal apparatus 322 to the first roller 324 and are positioned on the second surface 340 of the first substrate 306. In some configurations, the speed S2 is less than the speed S1, and as such, the elastic strands 316 are stretched in the machine direction MD.

With continued reference to FIG. 10, the second substrate 308 advances at speed S1 to the first roller 324 and partially wraps around the outer circumferential surface 326 of the first roller 324. In turn, the second substrate 308 is combined with the first substrate 306 and the stretched elastic strands 316 while on the first roller 324 such that the elastic strands 316 are joined with the second surface 340 of the first substrate 306 and the first surface 342 of the second substrate 308 to produce a continuous length of elastomeric laminate 302. As discussed above, the first substrate 306 may advance past an adhesive applicator device 348 that applies adhesive 350 to the second surface 340 of the first substrate 306 while advancing to the first roller 324. It is to be appreciated that the adhesive 350 may be applied to the first substrate 306 while the first substrate 306 is partially wrapped around the outer circumferential surface 326 of the first roller 324. It is to be appreciated that adhesive may also be applied to the elastic strands 316 before and/or while being joined with first substrate 306 and second substrate 308. In addition, it is to be appreciated that adhesive may be applied to the first surface 342 of the second substrate 308 before or while being joined with the elastic strands 316 and first substrate 306.

Figure 11:
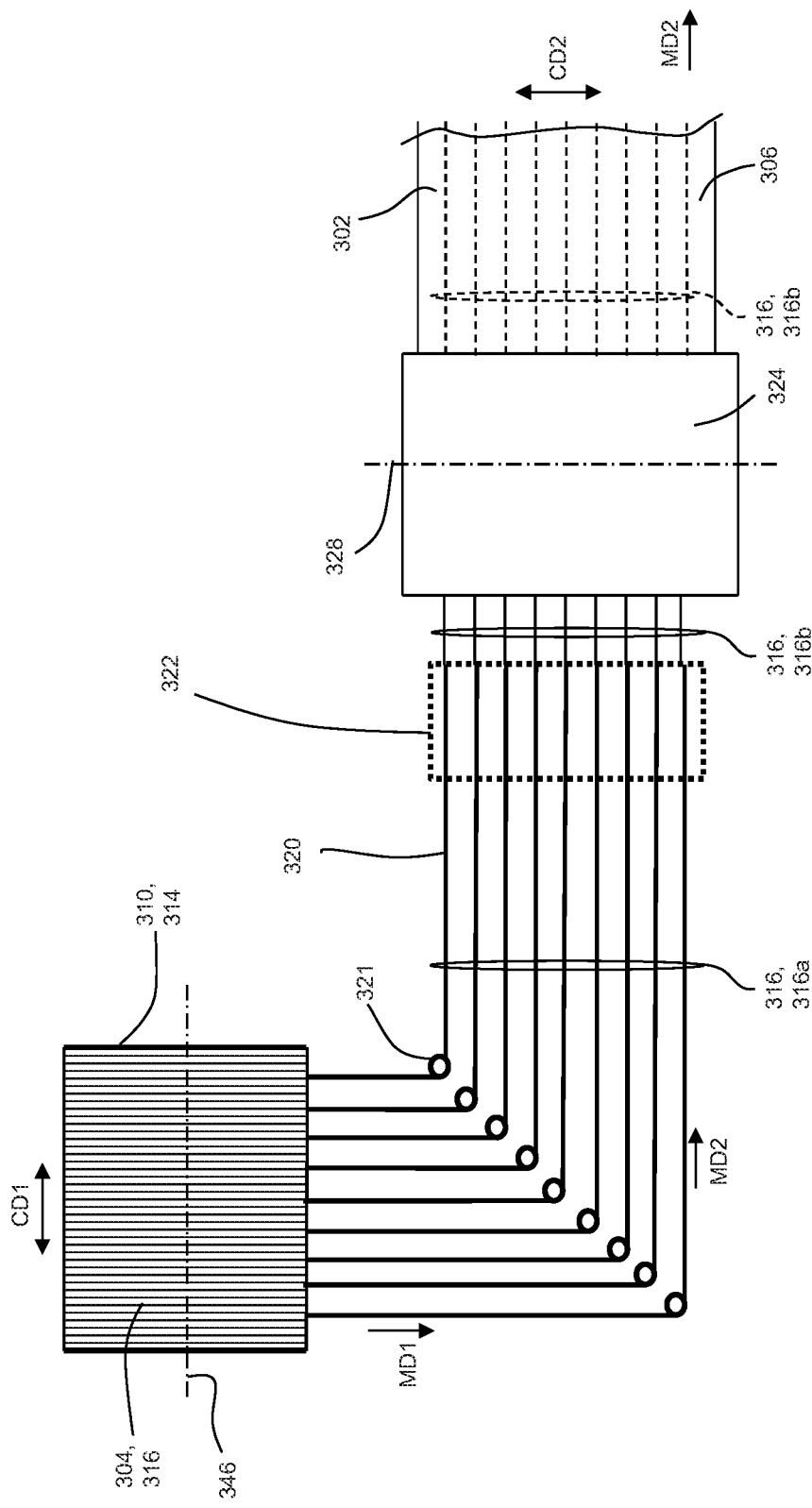
FIG. 11 is a schematic side view of a fourth configuration of a converting apparatus adapted to manufacture an elastomeric laminate including a spin finish removal apparatus.

As illustrated herein, the apparatuses and processes may be configured such that elastic strands may be advanced from the beams and directly to the assembly process without having to touch additional machine components, such as for example, guide rollers. It is also to be appreciated that in some configurations, elastic strands may be advanced from beams and may be redirected and/or otherwise touched by and/or redirected before advancing to the assembly process. For example, FIG. 11 shows a configuration where the beam rotation axis 346 may extend in a first cross direction CD1. As the beam 314 rotates, the elastic strands 316 advance from the beam 314 in a first machine direction MD1 with the elastic strands 316 being spaced apart from each other in the first cross direction CD1. The elastic strands 316 may then be redirected by rollers 321 from the first machine direction MD1 to a second machine direction MD2, wherein the elastic strands 316 may remain separated from each other in a second cross direction CD2. From the rollers 321, the elastic strands 316 may advance in the second machine direction MD2 to be combined with the first and second substrates 306, 308 to form the elastomeric laminate 302. Thus, it is to be appreciated that the beam 314 may be arranged and/or oriented such that the beam rotation axis 346 may be parallel, perpendicular, or otherwise angularly offset with respect to the machine direction advancement of the elastomeric laminate 302 and/or the substrates 306, 308.

The apparatus shown in FIG. 11 also includes a spin finish removal apparatus 322 generically illustrated by a dashed-line rectangle, which may be configured with various combinations of features of the spin finish removal apparatus 322 described herein. As discussed above, the spin finish removal apparatus 322 is configured to remove all or some of the spin finish 320 from the advancing elastic strands 316a. And in turn, the treated elastic strands 316b having some or all the spin finish 320 removed may advance downstream to be joined with the first substrate 306 and the second substrate 308. It is to be appreciated that the spin finish removal apparatus 322 may be positioned in various locations along the advancement path of the elastic strands 316. For example, the spin finish removal apparatus 322 may be positioned upstream or downstream of the rollers 321 shown in FIG. 11.

This application claims the benefit of U.S. Provisional Application No. 62/436,589, filed on Dec. 20, 2016; 62/483,965, filed on Apr. 11, 2017; 62/553,538, filed on Sep. 1, 2017; 62/553,149, filed on Sep. 1, 2017; 62/553,171, filed on Sep. 1, 2017; and 62/581,278, filed on Nov. 3, 2017, the entireties of which are all incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an elastomeric laminate, the method comprising steps of:
    providing an elastic strand wound onto a beam, wherein the elastic strand comprises a spin finish;
    rotating the beam to unwind the elastic strand from the beam;
    advancing the elastic strand from the rotating beam;
    applying a detergent to the elastic strand;
    advancing a first substrate at a first speed S1, and wherein the first substrate comprises a first surface and an opposing second surface;
    wiping a portion of the detergent and the spin finish from the elastic strand by advancing the elastic strand in contact with the second surface of the first substrate while advancing the elastic strand at a second speed S2, wherein $S1 \neq S2$;
    stretching the elastic strand; and
    connecting the stretched elastic strand between the first substrate and a second substrate subsequent to the step of wiping.

2. The method of claim 1, wherein the step of applying the detergent further comprises advancing the elastic strand through a bath of the detergent.

3. The method of claim 1, wherein the step of applying the detergent further comprises spraying the detergent onto the elastic strand.

4. The method of claim 1, wherein the step of applying the detergent further comprises wiping the detergent onto the elastic strand.

5. The method of claim 1, further comprising a step of drying the elastic strand subsequent to step of wiping.

6. The method of claim 5, wherein the step of drying the elastic strand further comprises moving air across the elastic stand.

7. The method of claim 1, wherein the step of stretching the elastic strand further comprises:
    advancing the first substrate at a first speed S1;
    rotating the beam to unwind the elastic strand from the beam at a second speed S2, wherein S2 is less than S1; and
    combining the elastic strand with the first substrate.

8. The method of claim 1, wherein the step of connecting the stretched elastic strand between the first substrate and the second substrate further comprises applying adhesive to at least one of the elastic strand, the first substrate, and second substrate.

* * * * *